United States Patent
Fukada et al.

[11] Patent Number: 6,065,329
[45] Date of Patent: May 23, 2000

[54] DEVICE AND METHOD FOR DETECTING LEAKAGE OF FILTER FILM

[75] Inventors: Seiji Fukada; Takao Itose, both of Nobeoka, Japan

[73] Assignee: Asahi Kasei Kogyo Kabushiki Kaisha, Osaka, Japan

[21] Appl. No.: 09/331,768

[22] PCT Filed: Dec. 25, 1997

[86] PCT No.: PCT/JP97/04828

§ 371 Date: Jun. 24, 1999

§ 102(e) Date: Jun. 24, 1999

[87] PCT Pub. No.: WO98/29184

PCT Pub. Date: Jul. 9, 1998

[30] Foreign Application Priority Data

Dec. 27, 1996 [JP] Japan .................................. 8-356628

[51] Int. Cl.[7] .............................. G01M 3/26; B01D 65/10
[52] U.S. Cl. ...................................................... 73/40; 73/37
[58] Field of Search .......................................... 73/37, 40

[56] References Cited

U.S. PATENT DOCUMENTS

| | | | |
|---|---|---|---|
| 5,417,101 | 5/1995 | Weich | 73/40 |
| 5,507,959 | 4/1996 | Glick | 73/40 X |
| 5,616,828 | 4/1997 | Kuczenski | 73/40 X |

FOREIGN PATENT DOCUMENTS

| | | | |
|---|---|---|---|
| 60-94105 | 5/1985 | Japan . | |
| 62-140607 | 6/1987 | Japan | 73/40 |
| 63-249569 | 10/1988 | Japan | 73/40 |
| 1-307409 | 12/1989 | Japan | 73/40 |
| 2-284035 | 11/1990 | Japan | 73/40 |
| 3-18373 | 1/1991 | Japan | 73/40 |
| 3-110445 | 5/1991 | Japan . | |
| 4-348252 | 12/1992 | Japan . | |
| 5-23551 | 2/1993 | Japan . | |
| 5-157654 | 6/1993 | Japan | 73/40 |
| 1518688 | 10/1989 | U.S.S.R. | 73/37 |

*Primary Examiner*—Daniel S. Larkin
*Attorney, Agent, or Firm*—Birch, Stewart, Kolasch & Birch, LLP

[57] ABSTRACT

An apparatus for detecting leakage through a filtration membrane which comprises a gas-supplying source for supplying a gas to one of two spaces formed by partition with the filtration membrane, a gas-detecting device for measuring the degree of leakage of the gas into the other space, and further preventing the undesirable influence of the supplied gas on the gas-detecting device.

7 Claims, 1 Drawing Sheet

DEVICE AND METHOD FOR DETECTING LEAKAGE OF FILTER FILM

This application is the national phase under 35 U.S.C. § 371 of PCT International Application No. PCT/JP97/04828 which has an International filing date of Dec. 25, 1997, which designated the United States of America.

TECHNICAL FIELD

The present invention relates to apparatus and method for detecting leakage through a filtration membrane which permit highly sensitive detection of minute defects (e.g. pinholes) present in the filtration membrane.

In detail, the present Invention relates to apparatus and method for detecting leakage through a filtration membrane, in which the influence of expansion of the filtration membrane caused by pressurization Is first excluded and then the flow rate of leaking gas is measured.

BACKGROUND ART

Membrane separation using a filtration membrane is employed in various fields as a substance separation method which is simple and consumes only a small amount of energy. The working principle of the membrane separation is such that) basically, substances are screened by filtration, depending on the size of pores present In the membrane. Therefore, a uniform desired pore size is important for performance characteristics of the membrane.

On the other hand, defects are produced in the filtration membrane in some cases during production or use of the filtration membrane. The most typical defect is a defect called pinholes. The pinholes are a small number of pores having a size larger than the desired pore size of the filtration membrane. If the pinholes are present, substances capable of passing through the pinholes are not screened, so that a desired substance in the filtrate is contaminated with the substances which should be essentially excluded. Thus, the separation efficiency is lowered.

As a method for detecting the pinholes, the minute defect of the filtration membrane, it is known to use a method which utilizes the surface tension of a liquid which comprises pressurizing with a gas one of two spaces formed by partition with the filtration membrane, filling the other with the liquid, applying such a pressure that the gas flows out through the pinholes but not through normal pores, measuring the flow rate of gas leaking from the pinhole portions, and thereby investigating the presence of the pinholes.

For example, JP-A-1-307409 discloses three measuring methods, i.e., a method of directly measuring the flow rate of a gas on the supply side (the starting solution side) after a definite time after the start of pressurization, a method of measuring the flow rate of a liquid pushed out by the gas, on hollow yarn side (the filtrate side), and a method of measuring the dropping of the liquid level on the hollow yarn side (the filtrate side)

In addition, JP-A-60-94105 discloses two measuring methods, i.e., a method of measuring a pressure change due to the leakage of a gas on the basis of a pressure decrease on the starting solution side, and a method of directly measuring the leakage of the gas (corresponding to the amount of the gas supplied) by means of a gas flowmeter attached on the starting solution side.

Further, JP-A-5-157654 discloses a method comprising providing an air-tight gas chamber on the filtrate side and measuring the leakage of the gas on the basis of a pressure increase on the side on which the gas leakage and inflow occurs.

However, when the pinholes are small in size or number, the degree of gas leakage is low, so that it is often difficult to directly measure a low gas flow rate with high precision using a measuring instrument in the direct measurement method for measuring the gas flow rate.

The method of measuring the amount of a liquid pushed out by the gas and the method of measuring a pressure change by providing a gas chamber on the liquid enclosure side permit indirect and high-precision measurement of a low gas flow rate but involve problems. For example, when the membrane expands remarkably due to pressurization or when a precise measurement is required in which the expansion of the membrane cannot be neglected: the precision of measurement is decreased because a liquid outflow or a pressure change, or both are caused by the expansion of the membrane simultaneously with those caused by gas leakage, and the outflow and/or pressure change caused by the expansion are usually undistinguishable from those caused by the gas leakage.

DISCLOSURE OF THE INVENTION

An object of the present invention is to improve an apparatus for detecting leakage through a filtration membrane and a method for the detection, i.e., to solve the problem of reduced measurement precision caused by the expansion of the filtration membrane by pressurization, by pressurizing with a gas one of two spaces formed by partition with a membrane to a pressure at which the gas does not flow out through normal pores, filling the other space with a liquid, and measuring the flow rate of gas leaking out through pinholes of the filtration membrane by measuring the flow rate of liquid pushed out by the gas or by providing a gas chamber on the liquid enclosure side and measuring a pressure change in the gas chamber.

The present inventor conducted various investigations on the above subject and consequently found the following: when there is provided a mechanism for first excluding the influence of the expansion of a filtration membrane by pressurization, the flow rate of gas leaking out through very small pinholes can be determined efficiently with high precision, regardless of the expansion of the filtration membrane by pressurization even if the degree of gas leakage is low because the pinholes are small in both size and number. Thus, the present invention has been accomplished.

The present inventor also found that the amount of a gas enclosed in the gas chamber can be automatically regulated by a detecting apparatus equipped with the above-mentioned mechanism and the above-mentioned detecting method, resulting in an increased precision of measurement.

That is, aspects of the present invention are as follows:
(1) An apparatus for detecting leakage through a filtration membrane which comprises a gas-supplying means for supplying a gas to one of two spaces formed by partition with the filtration membrane, a gas-detecting means for measuring the degree of leakage of the gas into the other space, and a means for preventing the undesirable influence of the supplied gas on said gas-detecting means.
(2) An apparatus according to the above item (1), wherein said gas-detecting means is a pressure-detecting means for measuring the degree of leakage of the gas in terms of a pressure change.
(3) An apparatus according to the above item (2), wherein the means for preventing the undesirable influence of the supplied gas on said gas-detecting means is a three-way valve.
(4) An apparatus according to the above item (2) or (3), wherein said pressure-detecting means is a microdifferential pressure gauge.

(5) A method for detecting leakage through a filtration membrane which comprises pressurizing with a gas one of two spaces formed by partition with the filtration membrane to a pressure at which the gas does not flow out through normal pores, filling the other space with an examining liquid, determining the flow rate of gas leaking out through pinholes of the filtration membrane, and thereby investigating the presence of the pinholes of the filtration membrane, wherein the flow rate of the leaking gas is measured after first excluding the influence of the expansion of the filtration membrane by the pressurization.

(6) A method according to the above item (5), wherein the filtration membrane is a virus-separating membrane.

(7) A method according to the above item (6), wherein the virus-separating membrane is a membrane made of regenerated cellulose.

BEST MODE FOR CARRYING OUT THE INVENTION

Figure 1:
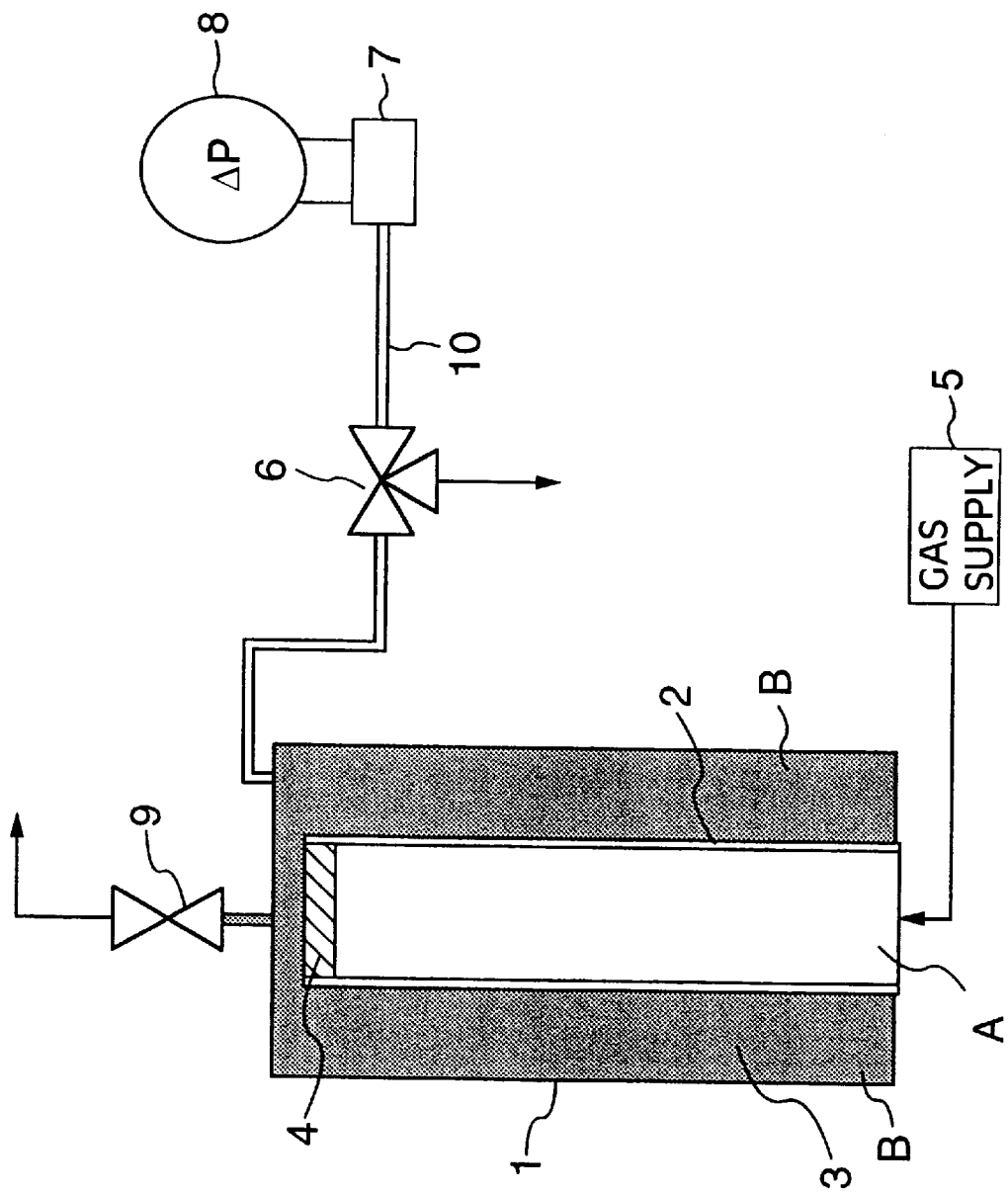
FIG. 1 is a schematic view of a typical example of the apparatus for detecting leakage through a filtration membrane of the present invention.

In the present invention, in order to, for example, detect minute defects (e.g. pinholes) of a filtration membrane, the filtration membrane is pressurized with a gas from one side (gas pressurization side). A space on the other side (liquid enclosure side) is filled with an examining liquid to wet the filtration membrane therewith. A small sealed gas space (a gas chamber) is provided on the liquid enclosure side. A pressure detector such as a micro-differential pressure gauge is connected to the gas chamber, and a slight pressure change caused by gas leaking out through defective portions of the filtration membrane is detected. In this case, a mechanism for detecting the minute defects is a combination of apparatus and method for detecting the slight pressure change caused by the leaking gas, though in the present invention, the detecting mechanism is not limited thereto and also includes, for example, apparatus and method for measuring the flow rate of liquid pushed out by the gas.

The present invention is characterized in that at the time of the pressurization with a gas in the leakage detection, a mechanism for removing a flow of the examining liquid caused by the expansion of the filtration membrane and a pressure increase caused by the flow in the portion filled with the examining liquid, such as, preferably, a three-way valve, is used to discharge the flow caused by the expansion of the filtration membrane and prevent the pressure increase, and that the capacity of the sealed gas space is kept constant by automatically filling the space between said filled portion and the three-way valve with the examining liquid. Because of these characteristics, even a slight leakage can be precisely detected.

In the present invention, the gas-supplying means includes, for example, a gas compressor and a gas cylinder. Usually, a gas obtained from such a source of compressed-gas supply is dehumidified and freed of dust by the use of a dehumidifier, a filter, etc., and adjusted with a pressure adjuster to a pressure at which said gas does not flow out through normal pores, and then the gas is introduced into a space on the gas pressurization side of a filtration membrane to be subjected to measurement, through a piping. When the examination is aseptically carried out, a gas sterilized by means of a filter or the like is supplied.

In the present invention, the gas-detecting means is, for example, a pressure-detecting means for measuring the degree of leakage of the gas in terms of a pressure change. As such a means, a pressure gauge suitable for the gas flow rate range and gas chamber capacity is properly selected depending on a filtration membrane to be subjected to measurement, in addition to a micro-differential pressure gauge.

In the present invention, in order to measure the gas flow rate, there may be carried out any of the following steps: the detection of a slight pressure change caused by leaking gas, the direct measurement of the gas flow rate, and the measurement of the flow rate of liquid pushed out by the gas.

In the present invention, the means for preventing the undesirable influence of the supplied gas on said gas-detecting means is a mechanism for excluding the influence of the membrane expansion and/or pressure. As such a means, two two-way valves may be used in addition to three-way valves.

The examining liquid used in the present invention, includes water, an aqueous sodium chloride solution, an alcohol solution, and the like. Their use depends on the kind and purpose of the membrane.

FIG. 1 shows an outline of the apparatus for detecting leakage through a filtration membrane of the present invention.

In FIG. 1, numeral 1 denotes a filter container having a filtration membrane built-in; numeral 2 denotes the filtration membrane having an edge face closed with a seal 4; numeral 5 denotes a source of pressurizing-gas supply for pressurizing the filtration membrane with a gas; numeral 3 denotes an examining liquid enclosed in a portion not to be pressurized with the gas in the filtration membrane container 1 partitioned with the filtration membrane 2, such as water; numeral 6 denotes a three-way valve connected to the liquid-enclosed portion of the filtration membrane container 1; numeral 7 denotes an air-tight gas chamber connected to the three-way valve; and numeral 8 denotes a differential pressure gauge connected to the gas chamber.

The seal 4 is not necessary in some cases, depending on the shape of the filtration membrane 2. It is sufficient that the filtration membrane container 1 is separated into a gas pressurization side A and a liquid enclosure side B by the filtration membrane 2.

Since the detection sensitivity is increased with, for example, a decrease of the capacity of the gas chamber 7, the gas chamber 7 also need not be positively attached if the capacity of an air-tight connecting piping 10 itself between the three-way valve 6 and the gas chamber 7 in FIG. 1 is sufficient as the capacity of a gas chamber.

The differential pressure gauge may be an ordinary pressure gauge, depending on the flow rate of leaking gas.

The filtration membrane 2 subjected to leakage detection by the method of the present invention is not particularly limited and may be any filtration membrane. The filtration membrane 2 includes, for example, micro-filtration membranes (microfilters, MF), reverse osmosis membranes, ultrafiltration membranes (UF), and virus-separating membranes. As to the shape of the membrane, any membrane, such as a plain membrane or a hollow-yarn membrane, can be examined in the present invention, irrespective of its shape.

Particularly in a regenerated-cellulose microporous membrane composed of a hollow-yarn membrane having a high virus-removing capacity and a high protein permeability, high-precision detection of pinholes is desired as a virus-separating membrane because of the high removing capacity required of the microporous membrane. The apparatus and method for detecting leakage of the present invention realizes such high-precision detection easily and efficiently.

A more specific example of the method for detecting leakage through a filtration membrane of the present invention is described below by taking the case of the apparatus for detecting leakage shown in FIG. 1.

(1) Preparatory stage

First, the three-way valve 6 is operated so that an outflow from the filtration membrane container 1 may be discharged outside the system as it is.

The space outside the filtration membrane 2 in the filtration membrane container 1 is filled with water as the examining liquid 3 for measurement. In this case, the space may be filled with water after detachment of the source of pressurizing-gas supply (on the gas pressurization side A) while filtering the examining liquid (water), or the space may be filled with water through an opened valve 9 over the filtration membrane container 1.

(2) Preliminary pressurization (the exclusion of the influence of membrane expansion)

The three-way valve 6 is kept in such a state that a gas outflow from the filtration membrane container 1 is discharged outside the system as it is.

The space inside the filtration membrane 2 is pressurized to ninety-eight kPa (one kg/cm$^2$) with a gas (air). When water is used as the examining liquid and air is used as the pressurizing gas, the pressurization pressure of ninety-eight kPa is a pressure at which when the contact angle is taken as one, the gas passes through pores with a diameter of about three microns or more but not through pores with a diameter of less than three microns. The filtration membrane examined for leakage in the present invention is, for example, a micro-filtration membrane (a microfilter, MF), reverse osmosis membrane, ultrafiltration membrane (UF), or virus-separating membrane. Since all the normal pores of any of these membrane have a diameter of less than three microns, air does not pass through the normal pores.

In this case, when the filtration membrane 2 is expanded or pinholes with a diameter of three microns or more are present, the examining liquid (water) and the pressurizing gas (air) are discharged outside the system through the three-way valve 6 by the leakage the pressurizing gas (air).

The expansion of the filtration membrane 2 is mostly an elastic change and terminates in a short time of one hundred eighty seconds or less.

(3) Pressure measurement

After a previously estimated expansion time of the membrane (one hundred eighty seconds), the three-way valve 6 is operated at the pressurized state manually or automatically with a timer so that the filter container 1 may communicate with the gas chamber 7.

In this case, if the degree of expansion (volume) of the filtration membrane 2 remarkably exceeds the degree of leakage (volume) of the gas (air), the space between the filtration membrane container 1 and the three-way valve 6 is automatically filled with the examining liquid 3 (water), and the capacity of the gas chamber 7 is always kept constant as the total capacity of the gas chamber itself and the connecting piping 10 between the gas chamber and the three-way valve, so that the extent of errors in the pressure change measurement produced by a change in capacity of the gas chamber is reduced, resulting in an improved precision of measurement.

A pressure increase in a definite time thirty seconds) after the operation of the three-way valve is measured with the differential pressure gauge 8.

(4) Judgement

The pressure measured may be used as it is as a measured value or may be converted to a flow rate on the basis of the capacity of the gas chamber 7.

Even in the case of a normal filtration membrane free from leakage, measured values are usually not zero owing to, for example, gas diffusion. Therefore, the average and the scatter of measured values are determined, and the thus obtained value is compared with a value measured for a filtration membrane examined for leakage, whereby the occurence of leakage through this filtration membrane can be determined.

EXAMPLE 1

By the use of an apparatus having the structure shown in FIG. 1, results obtained by carrying out preliminary pressurization (the exclusion of the influence of membrane expansion) were compared with those obtained without preliminary pressurization, by using each of filters having pinholes and filters having no pinholes. As the filters subjected to measurement, there were used filters with an average pore diameter of fifteen nm and a membrane area of one m$^2$ (PLANOVA, a registered trade name, mfd. by Asahi Kasei Kogyo K.K.).

As the measurement conditions, the pressurization time and the pressure measurement time were one hundred eighty seconds and thirty seconds, respectively, in the case of carrying out the preliminary pressurization and were three seconds and thirty seconds, respectively, in the case of not carrying out preliminary pressurization. In both cases, the capacity of the gas chamber was adjusted to sixteen cc (ml).

As to a measuring procedure, the three-way valve 6 (mfd. by COSMO INSTRUMENT CO., LTD.) was operated at first in a preparatory stage so that an outflow from the filtration membrane container 1 might be discharged outside the system as it was. Then, water is introduced into the space outside the filtration membrane in the filtration membrane container 1 from the opened valve 9 over the filtration membrane container 1 to fill the space with water. Subsequently, the space inside the filtration membrane 2 was pressurized to ninety-eight kPa (one kg/cm$^2$) with a gas (air) while keeping the three-way valve 6 in such a state that the outflow from the filtration membrane container 1 was discharged outside the system as it was. When the preliminary pressurization was carried out (when the influence of membrane expansion was excluded), this condition was maintained for one hundred eighty seconds. When no preliminary pressurization was carried out, the condition was maintained for three seconds. After the maintenance of said condition, the three-way valve was operated so that the filter container 1 might communicate with the gas chamber 7, and pressure measurement was carried out.

A pressure increase value thirty seconds after the operation of the three-way valve was measured with the differential pressure gauge 8 (mfd. by COSMO KEIKI K.K.).

As the filters having pinholes, there were used two filters, i.e., a filter having relatively remarkable pinholes and a filter having relatively slight pinholes. For both filters having pinholes, the production of bubbles through the filtration membrane 2 could be found by visual observation when in FIG. 1, the space on the liquid enclosure side B was filled with water and the space on the pressurization side A was pressurized to ninety-eight kPa with air. In this case, a large amount of bubbles were produced through the filter having relatively remarkable pinholes, and bubbles were also produced through the filter having relatively slight pinholes. On the other hand, in the case of the filters having no pinholes, no bubbles were produced at all when in FIG. 1, the space on the liquid enclosure side B was filled with water and the space on the pressurization side A was pressurized to ninety-eight kPa with air.

Table 1 shows pressure change values obtained in a measurement time of thirty seconds in the case of not carrying out preliminary pressurization (pressurization time: three seconds), and Table 2 shows pressure change values obtained in a measurement time of thrity seconds in the case of carrying out the preliminary pressurization (pressurization time: one hundred eighty seconds). In the tables, the symbols for the filters $F_A$, $F_B$, and $F_C$ denote the filters having no pinholes, $F_D$ denotes the filter having relatively remarkable pinholes, and FE denotes the filter having slight pinholes. In Table 2, for the filters having pinholes $F_D$ and $F_E$, the pressure change values were calculated according to the rule of three because they exceeded the upper limit of measurement in about 1.5 seconds.

TABLE 1

When no preliminary pressurization was carried out.

|  | $F_A$ | $F_B$ | $F_C$ | $F_D$ | $F_E$ |
|---|---|---|---|---|---|
| Pressure change value (Pa) | 4900 | 4508 | 3038 | 28028 | 7644 |

TABLE 2

When preliminary pressurization was carried out.

|  | $F_A$ | $F_B$ | $F_C$ | $F_D$ | $F_E$ |
|---|---|---|---|---|---|
| Pressure change value (Pa) | 2793 | 2999 | 3067 | 19600 | 19600 |

In both Table 1 and Table 2, the pressure change was greater in the case of the two filters having pinholes $F_D$ and $F_E$ than in the case of the three filters having no pinholes $F_A$, $F_B$, and $F_C$. However, there was a large difference between the measurement sensitivity attained when no preliminary pressurization was carried out and that attained when the preliminary pressurization was carried out. Table 3 shows the difference between a mean value obtained for filters having no pinholes and each measured value for the filter having pinholes.

TABLE 3

| Statistic | | No preliminary pressurization | Preliminary pressurization (180 sec.) |
|---|---|---|---|
| No pinholes | Mean of pressure change (Pa) | 4149 | 2953 |
|  | Standard deviation of pressure change (Pa) | 982 | 143 |
| Pinholes were present | Measured value for filter $F_E$ | 7644 | 19600 |
| Difference between mean value for filters having no pinholes and measured value for filter having pinholes (Pa) | | 3495 | 16647 |
| (Difference from mean value for filters having no pinholes)/standard deviation | | 3.6 | 116 |

When the difference between a mean value obtained for the filters having no pinholes and a pressure change value measured for the filter having pinholes is four to five times or more as large as the standard deviation, the presence of pinholes can be conventionally determined. However, the presence of pinholes in the filter $F_E$ could not be clearly determined without preliminary pressurization because said difference is small. On the other hand, when the preliminary pressurization for one hundred eighty seconds was carried out in the case of one and the same filter $F_E$, the employment of the mechanism for removing a pressure change due to the membrane expansion results in a sufficiently large difference between a mean value obtained for the filters having no pinholes and a pressure change value measured for the filter having pinholes, so that the presence of pinholes in the filter $F_E$ could be sufficiently determined. As a result of carrying out the preliminary pressurization for one hundred eighty seconds to exclude the influence of the membrane expansion, both the absolute values of pressure change and the scatter of the values expressed in terms of a standard deviation were reduced. Consequently, the difference between the mean value obtained for the filters having no pinholes and the pressure change value measured for the filter having pinholes was widened, resulting in an increased detection sensitivity.

According to the present invention, the influence of the expansion of a filtration membrane by pressurization is previously excluded by means of a three-way valve or the like, so that a slight gas leakage through a filtration membrane having minute defects such as pinholes can be detected with high precision even if the filtration membrane is expanded. Therefore, even very small pinholes or a small number of pinholes of the filtration membrane can be detected with high sensitivity.

We claim:

1. An apparatus for detecting leakage through a filtration membrane which comprises a gas-supplying means for supplying a gas to one of two spaces formed by partition with the filtration membrane, a gas-detecting means for measuring the degree of leakage of the gas into the other space, and a means for preventing the undesirable influence of the supplied gas on said gas-detecting means.

2. An apparatus according to claim 1, wherein said gas-detecting means is a pressure-detecting means for measuring the degree of leakage of the gas in terms of a pressure change.

3. An apparatus according to claim 2, wherein the means for preventing the undesirable influence of the supplied gas on said gas-detecting means is a three-way valve.

4. An apparatus according to claim 2 or 3, wherein said pressure-detecting means is a micro-differential pressure gauge.

5. A method for detecting leakage through a filtration membrane which comprises pressurizing with a gas one of two spaces formed by partition with the filtration membrane to a pressure at which said gas does not flow out through normal pores, filling the other space with an examining liquid, determining the flow rate of gas leaking out through pinholes of the filtration membrane, and thereby investigating the presence of the pinholes of the filtration membrane, wherein the flow rate of the leaking gas is measured after first excluding the influence of the expansion of the filtration membrane by the pressurization.

6. A method according to claim 5, wherein the filtration membrane is a virus-separating membrane.

7. A method according to claim 6, wherein the virus-separating membrane is a membrane made of regenerated cellulose.

* * * * *